(12) United States Patent
Ferreira et al.

(10) Patent No.: US 10,499,995 B2
(45) Date of Patent: Dec. 10, 2019

(54) NAVIGATION BY BENDING FORCES

(71) Applicant: THE UNIVERSITY OF WESTERN ONTARIO, London (CA)

(72) Inventors: Louis Ferreira, London (CA); Matthew Stokes, London (CA)

(73) Assignees: Louis Ferreira, London, Ontario (CA); Matthew Stokes, San Francisco, CA (US)

( * ) Notice: Subject to any disclaimer, the term of this patent is extended or adjusted under 35 U.S.C. 154(b) by 119 days.

(21) Appl. No.: 15/547,859

(22) PCT Filed: Jan. 27, 2016

(86) PCT No.: PCT/CA2016/050064
§ 371 (c)(1),
(2) Date: Aug. 1, 2017

(87) PCT Pub. No.: WO2016/123697
PCT Pub. Date: Aug. 11, 2016

(65) Prior Publication Data
US 2018/0014887 A1    Jan. 18, 2018

Related U.S. Application Data

(60) Provisional application No. 62/110,935, filed on Feb. 2, 2015.

(51) Int. Cl.
*A61B 34/20* (2016.01)
*G01L 5/00* (2006.01)
(Continued)

(52) U.S. Cl.
CPC .............. *A61B 34/20* (2016.02); *A61B 34/30* (2016.02); *A61B 34/77* (2016.02); *B25J 9/1633* (2013.01);
(Continued)

(58) Field of Classification Search
CPC .......... A61B 34/20; A61B 34/77; A61B 34/30; A61B 2034/2046; A61B 2034/2061;
(Continued)

(56) References Cited

U.S. PATENT DOCUMENTS 7,862,570 B2 * 1/2011 Russell .................. A61B 34/20
                                                              600/424
8,448,514 B2   5/2013 Hartmann et al.
(Continued)

FOREIGN PATENT DOCUMENTS

CA          1139404        11/1983
CA          2555473         1/2005
(Continued)

OTHER PUBLICATIONS

International Search Report (PCT/CA2016/050064) dated Apr. 22, 2016.
(Continued)

*Primary Examiner* — Jaime Figueroa
(74) *Attorney, Agent, or Firm* — Hill & Schumacher (57) ABSTRACT

The present disclosure provides a navigation method and system which does not require a remotely located tracking system, or additional targets or other devices to be installed on the patient or object being tracked. The system uses one flexible component in physical contact with the patient/object and measures relative position as a function of forces that are generated by the flexing component as it is bent. The system translates forces into navigational commands for a robot, other manipulator, or for human manual navigation. A method for transforming a pre-planned motion pathway into a sequence of forces for this mode of navigation is also described. This system is also applicable in the field of manufacturing robotics, where the locations of objects or assemblies may not be precisely known or constant. The
(Continued)

method and system disclosed herein can be used to maintain known position of an object/assembly or to navigate movement of a robot relative to an object/assembly as in the case of machining.

28 Claims, 6 Drawing Sheets (51) Int. Cl.
- B25J 9/16 (2006.01)
- A61B 34/00 (2016.01)
- G05D 1/10 (2006.01)
- A61B 34/30 (2016.01)
- A61B 90/00 (2016.01)
- G01L 5/22 (2006.01)

(52) U.S. Cl.
CPC ........... *B25J 9/1694* (2013.01); *G01L 5/0057* (2013.01); *G05D 1/10* (2013.01); *A61B 2034/2046* (2016.02); *A61B 2034/2061* (2016.02); *A61B 2090/064* (2016.02); *G01L 5/228* (2013.01); *G05B 2219/37403* (2013.01); *G05B 2219/39218* (2013.01)

(58) Field of Classification Search
CPC . A61B 2090/064; B25J 9/1694; B25J 9/1633; G05D 1/10; G01L 25/00; G05B 2219/37403; G05B 2219/39218
USPC .................................................. 700/245, 253
See application file for complete search history.

(56) References Cited

U.S. PATENT DOCUMENTS

| | | | |
|---|---|---|---|
| 8,504,500 | B2 | 8/2013 | Hartmann et al. |
| 8,597,178 | B2 | 12/2013 | Yoshie |
| 9,092,737 | B2 | 7/2015 | Hartmann et al. |
| 10,022,192 | B1* | 7/2018 | Unnnnalaneni ........ A61B 34/20 |
| 2007/0156019 | A1* | 7/2007 | Larkin .................... B25J 19/025 600/104 |
| 2010/0332030 | A1* | 12/2010 | Larkin .................... G01L 5/226 700/245 |
| 2011/0184406 | A1* | 7/2011 | Selkee ................. A61B 5/6885 606/41 |
| 2013/0345718 | A1 | 12/2013 | Crawford et al. |
| 2015/0119638 | A1 | 4/2015 | Yu et al. |
| 2016/0029960 | A1* | 2/2016 | Toth ................... A61B 18/1492 600/301 |
| 2017/0273712 | A1* | 9/2017 | Carlson .............. A61B 10/0283 |
| 2017/0333052 | A1* | 11/2017 | Ding ...................... A61B 34/20 |
| 2017/0348061 | A1* | 12/2017 | Joshi .................. A61B 17/7089 |
| 2018/0014891 | A1* | 1/2018 | Krebs ................... A61B 17/15 |

FOREIGN PATENT DOCUMENTS

| | | |
|---|---|---|
| CA | 2652245 | 11/2007 |
| WO | 2015070343 | 5/2015 |

OTHER PUBLICATIONS

Written Opinion (PCT/CA2016/050064) dated Apr. 22, 2016.
Bebek et al. "Whisker-Like Position Sensor for Measuring Physiological Motion" IEEE/ASME Transactions on Mechatronics, Oct. 2008 vol. 13, No. 5 pp. 538-547.

* cited by examiner

NAVIGATION BY BENDING FORCES

FIELD

The current disclosure relates to a navigation method and system (also referred to as navigation by bending forces and Nav-by-Bending-Forces), with applications in surgical applications and manufacturing and other fields requiring positional navigation through relatively short distances.

BACKGROUND

A tracking system in surgery is required in order to navigate a pre-operative plan relative to the patient's anatomy. The tracking system is generally used to track the patient's anatomy during the surgery and to navigate hand-operated surgical tools or a robot-assisted surgical tool.

Current surgical tracking systems in use rely upon determining the poses (position and orientation) of targets, such as infrared-emitting diodes or retroreflective spheres, which are attached to instruments or fixed into bone. An industry leader in producing such systems is NDI who have a medical product line consisting of two families of tracking systems, namely Polaris and Aurora. Details of the Polaris system can be found at: http://www.ndigital.com/medical/products/polaris-family/. The Polaris tracking system tracks the 3D position and orientation of active or passive markers attached to surgical tools with optical measurement technology. Details of the Aurora system can be found at: http://www.ndigital.com/medical/products/aurora/.

However, there are several significant drawbacks to current systems for tracking patient anatomy. Current optical tracking systems require a clear line of sight in order to "see" their targets. Optical tracking systems can be obtrusive and interfere with the surgical workflow because surgical staff must not occlude the camera's line of sight. These cameras are normally mounted at some distance from the patient. As the surgical working area is already somewhat small and compact, this makes it very difficult for surgical staff to work without blocking the cameras. This is perhaps the reason that is most noted by surgeons who express why navigation and robot-assisted systems are not adopted for most procedures in which they could be of value.

Also, many current intra-operative tracking systems require tracking devices to be rigidly mounted to the patient's bones of interest. This means that stab incisions are made in order to gain access to bone so that tracking targets can be drilled into the bones. These installation sites are most often not part of the surgical incision and exposure. Thus, they are considered to be additional morbidity which must be healed, and sources for increased risk of infection.

Cost also plays a significant role in the adoption of surgical systems. There are three elements of cost including initial capital cost (current tracking systems can easily cost $100,000 or more), replacement and maintenance costs, including sterilization and the cost of operating room time. Thus, cost is a significant factor for smaller and more remote medical establishments.

The tracking targets of current tracking systems require occasional replacement due to breakage and wear from being inside of the surgical field. Many popular optical trackers use passive retro-reflective targets that must be discarded and replaced after each surgery, which accounts for significant waste and expense. Additionally, the re-usable electronic targets and their bone mounting hardware must be sterilized using means that are safe to electronic equipment. Each of these targets has at least two parts for bone mounting and also require batteries which must be replaced for each surgery.

Most surgical procedures can begin immediately following incision and exposure. However, the most common surgical tracking systems are optical and require some setup of the camera for line of sight, and significant setup of the tracking targets for installation into bone, as described in above. This adds significant operating room time, which increases costs significantly to hospitals and the healthcare system. Tracking systems that are not optical, such as electromagnetic or ultrasonic, still require installation of targets, receivers or emitters in anatomy as described above.

Most current tracking technologies have fixed resolutions. For example, optical systems, which are the most commonly used tracking technology, have camera chips with a fixed number of pixels and pixel dimensions. Moreover, all current tracking systems navigate by position/orientation, which requires mathematical reduction to position coordinate and orientation angles, or geometric fitting such as least squares algorithms. These methods require complex calibration, and induce measurement error.

All current tracking systems, be they electromagnetic, optical, or ultrasonic are susceptible to interference from one or more electromagnetic, radio, sonic, or light sources. In particular, electromagnetic systems can also be impacted by metal surgical tools, operating table, and other metallic objects.

It would be very advantageous to provide a surgical navigation system which avoids the above-mentioned limitations and drawbacks and provides an economically cheaper alternative to current surgical navigation systems.

SUMMARY

In the present disclosure, a navigation method and system is described which does not require a remotely located tracking system, or additional targets or other devices to be installed on the patient or object being tracked. The system uses one flexible component in physical contact with the patient/object and measures relative position as a function of forces that are generated by the flexing component as it is bent. The system translates forces into navigational commands for a robot, other manipulator, or for human manual navigation. A method for transforming a pre-planned motion pathway into a sequence of forces for this mode of navigation is also described.

This system is also applicable in the field of manufacturing robotics, where the locations of objects or assemblies may not be precisely known or constant. The method and system disclosed herein can be used to maintain known position of an object/assembly or to navigate movement of a robot relative to an object/assembly as in the case of machining.

Thus, in an embodiment there is provided a system for tracking an object, comprising:

a) a motive source, an instrument attachable at a proximal end thereof to the motive source and movable by the motive source;

b) a load cell fixed in a known position with respect to the proximal end of the instrument when it is attached to the motive source;

c) a flexible component having a proximal end attached to the load cell, the flexible component having a distal end configured to make physical contact with an object being tracked; and d) a computer controller connected to the load cell for receiving an output from the load cell, said output from said load cell including forces that are generated by the flexible component as it is bent when said object moves, the computer controller programmed with instructions to translate said forces that are generated by the flexible component into navigational commands for said motive force to maintain said instrument in a preselected pose with respect to said object.

In another embodiment there is provided a system of navigation of an object, comprising:

a) a motive source, an instrument attachable at a proximal end thereof to said motive source and movable by said motive source;

b) a load cell fixed in a known position with respect to said proximal end of said instrument when it is attached to said motive source;

c) a flexible component having a proximal end attached to said load cell, said flexible component having a distal end configured to make physical contact with an object being tracked; and d) a computer controller connected to said load cell and pre-programmed with a navigation algorithm containing a pre-selected navigation route, wherein said computer controller is programmed with instructions to translate said navigation route into a series of predicted forces experienced by the flexible component calculated at discrete intervals along its predicted deformed configurations according to the pre-selected navigation route, and wherein said computer controller is programmed with an algorithm which inputs this series calculated forces into an input of the navigation algorithm.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. The drawings are not to scale.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein, the phrase "load cell" refers to a transducer that is used to create electrical signals whose magnitudes are directly proportional to the forces and torques being measured. These forces and torques are produced as reaction forces through a flexible component which is attached to the load cell at one end and in contact with an object to be tracked at the other end.

As used herein, the phrase "flexible component" means any object whose modulus of elasticity allows that the forces experienced are within the object's elastic range so as not to damage or plastically deform the object. Examples include a light metal strip, rubber or flexible composite, spring-loaded assembly, etc. Any custom-designed fixture or assembly can suffice as long as it has a flexible section with enough elastic range to satisfy the flexural working range required by the application.

As used herein, the word "pose" means a combination of position and rotation values, which together, represent a discrete location and orientation of an object.

The navigation system disclosed herein, referred to herein as the navigation by bending forces system, is designed to provide movement tracking and robotic end-effector positioning guidance without the reliance on a secondary tracking system. In addition to robotic navigation feedback, it can be used for a simpler positioning device, or even a hand-operated tool. For simplicity, the navigate-by-bending-forces system will be described for robotic use from this point forward, however it will be understood that it may be used in non-robotic applications and the same principles of operation would be generally the same.

Figure 1:
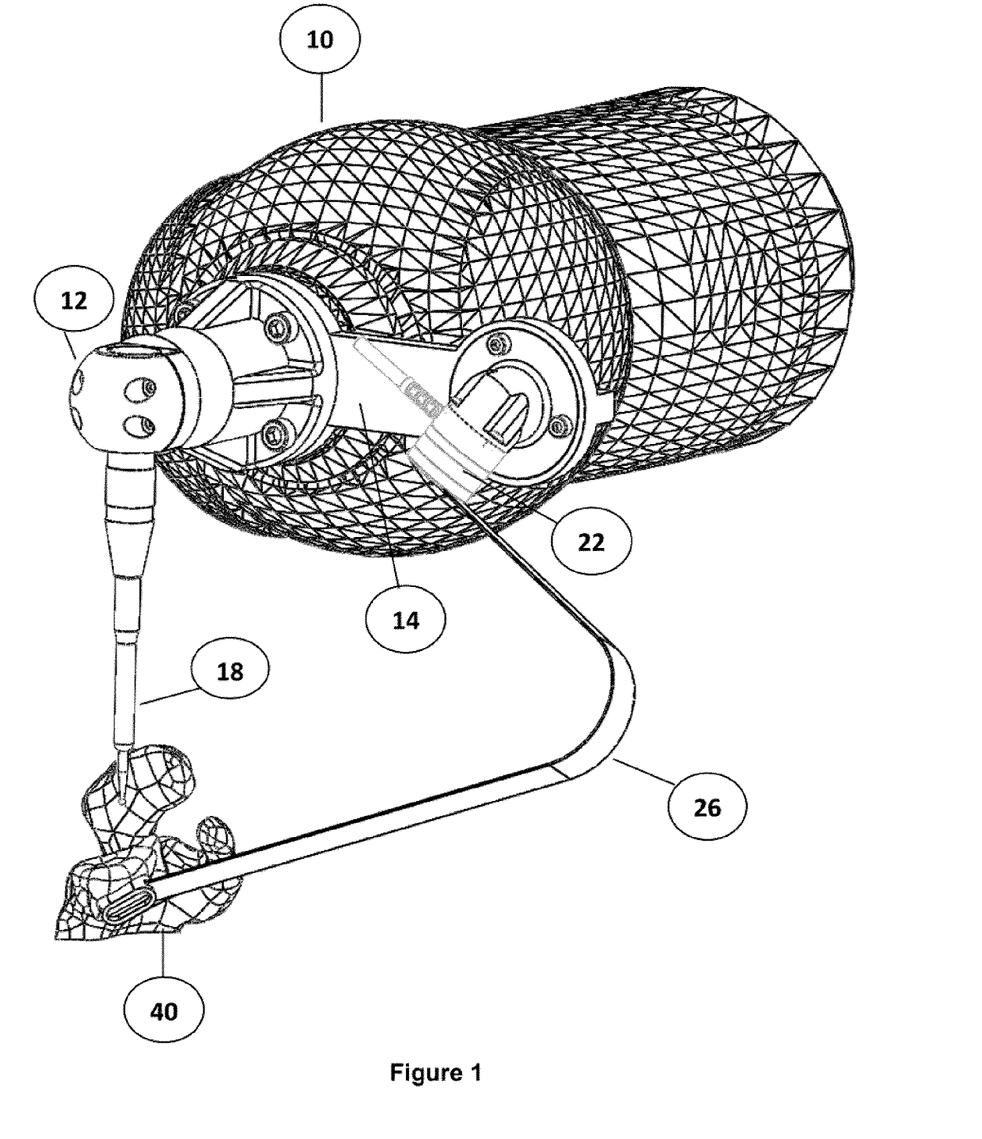
FIG. 1 illustrates the surgical tracking system using navigation by flexible component.

Referring to FIG. 1, a robotic arm shown generally at 10 includes an end effector 12 mounted on the distal end of arm 10. End effector 12 includes a base plate 14 to which a surgical tool/instrument, or manipulator 18 is attached. A load cell 22 is mounted to the end effector 12, rigidly with respect to the tool/instrument/manipulator 18, such that there is no relative motion between the load cell 22 and tool/instrument/manipulator 18.

Figure 2:
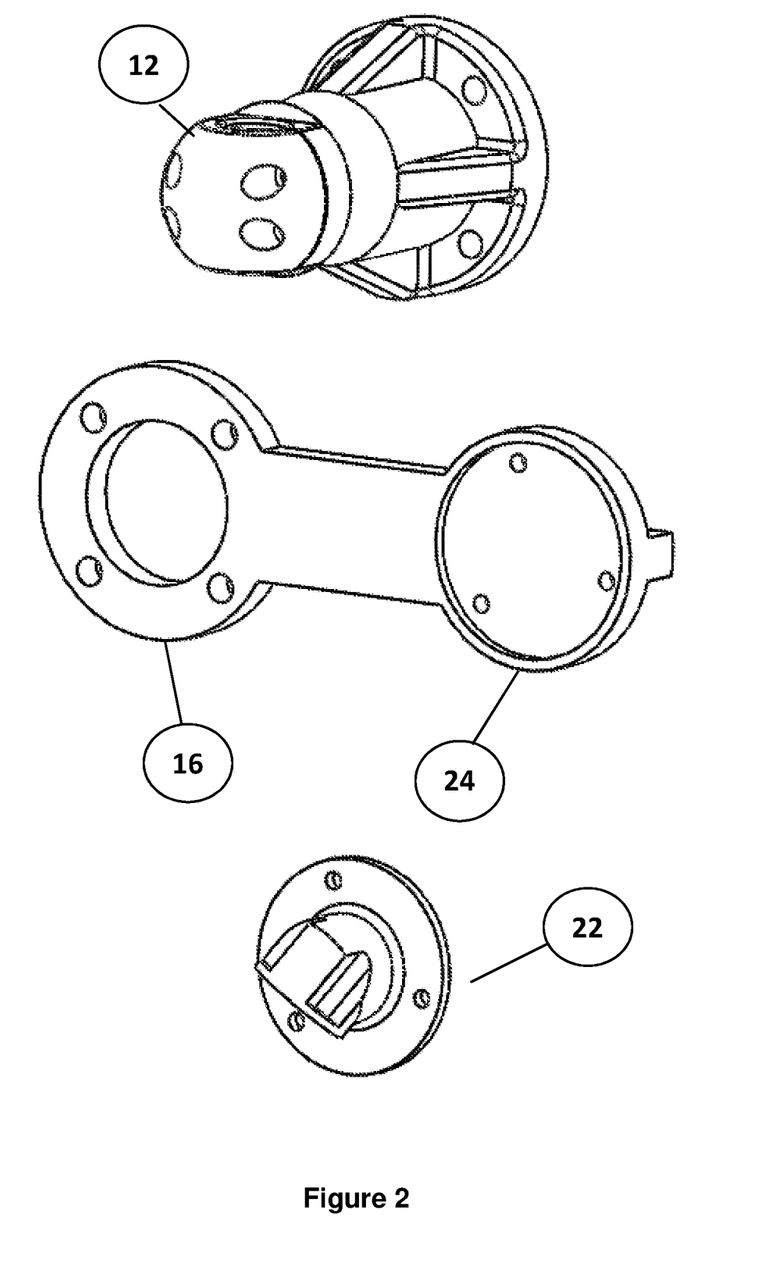
FIG. 2 shows perspective views of a tool holder, a load cell and a mounting bracket for mounting the load cell and the tool to the tool holder.

Referring to FIG. 2, the load cell 22 is positioned off center out of the way of the tool profile of the tool 18 being used, this being accomplished using base plate 14 which is configured to include two spaced mounts 16 and 24 spaced by a rigid middle section with end effector 12 mounted to mount 16 and load cell 22 mounted to mount 24. A flexible component 26 is mounted at its proximal end to the free end of the load cell 22. The distal end or mounting surface of the flexible component 26 is in physical contact with the object 40 (which may any object or in the case of a surgical procedure it may be patient anatomy 40 to be tracked). The load cell 22 measurement system outputs voltages proportional to forces and torques experienced by the flexible component 26 to off board computer 30. The flexible component 26 allows relative movement between the object/patient being tracked and the tool/instrument/manipulator 18, as well as the load cell 22. This relative movement corresponds to flexure in the flexible component 26 consisting of forces and torques, which are measured by the load cell 22 and transmitted as proportional voltages in real-time to the control system.

Figure 3:
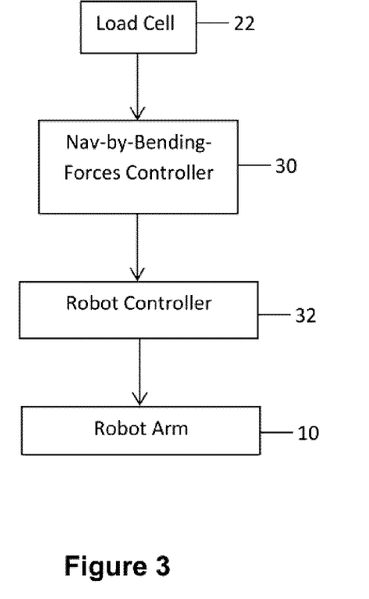
FIG. 3 shows a block diagram of an embodiment the present system including a real time monitor processor connected to a load cell and a robot control processor and the robot control processor connected to the robotic arm.

FIG. 3 shows a block diagram of the present system shown generally at 20 which includes a real time monitor computer processor 30 connected to load cell 22 and a robot controller 32 and the robot controller connected to the robotic arm 10. In some robot applications, depending on the robot manufacturer's controller implementation, there can be an embodiment that does not include a separate robot controller, or the robot controller 32 may reside in the same processor as the Nav-by-Bending-Forces controller 30.

Figure 4:
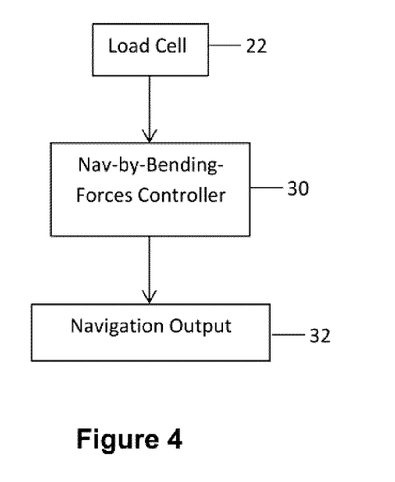
FIG. 4 shows a block diagram of another embodiment the present system including a real time monitor processor connected to a load cell but in which a robot is not used, but rather a human moves the tool by hand.

FIG. 4 shows another embodiment in which a robot is not used, but rather a human moves the tool by hand. In this embodiment, the navigation commands of the Nav-by-Bending-Forces controller are output to a display, or other type of human machine interface, such as an acoustic or haptic device. In any case, a human can be navigated by translating the navigation commands of the controller 30 into application-specific feedback signals.

The navigation by bending forces controller/processor 30 is programmed with a feedback control algorithm. The load cell 22 and control algorithm can be used to command robot arm 10 or other motion device, or to navigate a hand held tool/instrument. As mentioned above, voltage readings acquired by the controller/processor 30 are run through a calibration transformation matrix and are converted to force values. The force values represent the loads currently experienced by the flexible component. By biasing the load cell 22 in a starting position, changes in force values can be interpreted as relative movement between the object 40 being tracked and the robot's end-effector. Incremental position/orientation adjustments can be commanded to the robot 10 to compensate for the object's (40) movement. In addition, a planned motion path can be transformed into a planned sequence of bending forces and torques. This can then be used to move the robot in the planned path relative to the biased reference position and relative to the object. Motion or navigation is commanded by small correcting motion vectors in any or simultaneously all of six degrees of movement (i.e. linear movements in three Cartesian axis directions and rotations about the same axes). In the case of human navigation, in which the tool 18 is moved by hand, the commands can be displayed visually or using some other feedback modality such as audible signals or haptics.

Figure 5:
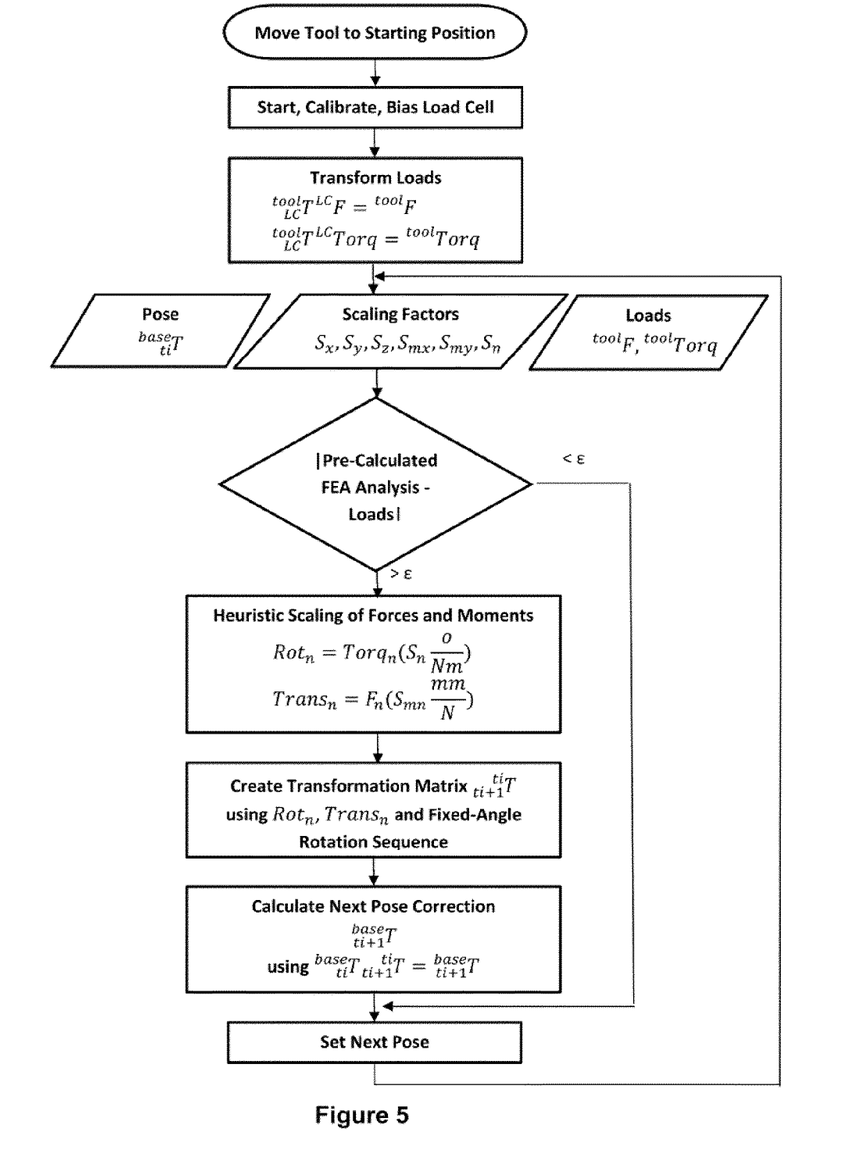
FIG. 5 shows a flow chart for a non-limiting implementation of the method disclosed herein.

The algorithm, described in more detail with respect to the flow chart of FIG. 5, includes a set of spatial transformations, which convert the forces/torques from the flexible object (measured by the load cell) into spatial corrections whose magnitudes are proportional to the measured forces/torques, such that greater errors in relative position inputted to the controller lead to greater magnitudes of spatial corrections to the relative position. The spatial corrections are also scaled to magnify or attenuate the position corrections and to tune the response performance. Each of six scaling factors, corresponding to the six degrees of movement spatial corrections, are adjusted in real-time in order to compensate for changing conditions (i.e. object/patient movement or other unknowns) and to minimize relative position errors. The real-time adjustment of scaling factors is currently accomplished using one Proportional Integral Derivative (PID) algorithm for each scaling factor corresponding to each degree of movement. A previous prototype of the robot control embodiment uses a heuristic decision-based algorithm to adjustment the scaling factors, by selecting a different magnitude for each scaling factor as a function of the input error magnitude. These are two examples of methods for adjusting the scaling factors; however, any method may be used which can adjust a value, or vector or array of values, as a function of a rising or falling error input. For example, fuzzy logic may also be used for this purpose. As the final navigation commands may be output as jogging events to the robot or other device or human, then modulation methods may also be used instead of continuous adjustment methods. The purpose of adjusting the scaling factors is to improve performance by reducing lag or delay. If this is not required, or if the robot, motion device or human task is sufficiently responsive, then an embodiment with only fixed scaling factors, or even none at all (i.e. equal to 1), may be used. The Nav-by-Bending-Forces algorithms may be encoded in software or in hardware. An exemplary and non-limiting implementation of the method is seen in the algorithm shown in the flowchart of FIG. 5.

The above-mentioned algorithm will be discussed in more detail with specific reference to the flow chart in FIG. 5. The algorithm involves transforming the force-torque (FT) output of the load cell (LC) to the tool coordinate system (CS), either by using the load cell's software or by the following transformation:

For force vector: $_{LC}^{tool}T^{LC}F = {}^{tool}F$ where F is the force vector $F = (F_x, F_y, F_z)$ For torque vector: $_{LC}^{tool}T^{LC}Torq = {}^{tool}Torq$ where Torq is the force vector $Torq = (Torq_x, Torq_y, Torq_z)$ Now the FT output is relative to the tool CS.

We need to get a transformation of the current tool's pose (ti) to a new tool pose (ti+1) relative to the base frame which reduces the FT. This is:

$$_{ti}^{base}T_{ti+1}{}^{ti}T = {}_{ti+1}^{base}T$$

Thus, we need a transformation $_{ti+1}{}^{ti}T$ that represents the new tool pose (ti+1) relative to the current tool pose (ti). This will be constructed from the FT transformation above. Say the rate of correction is set at 1 mm/N for forces and at 1°/Nm for torques, then for forces:

$$Trans_x = F_x \left(1 \frac{mm}{N}\right)$$

and similarly for the y and z directions. Note the sign is (+) to move in the force direction to relieve the force. Also note that the rate can be different for each direction. It can also be given a lower threshold to remove jitter near zero, and an upper limit to avoid large corrections.

For torques:

$$Rot_x = Torq_x \left(1 \frac{o}{Nm}\right)$$

and the same notes apply similarly as for corrective translations.

Now build a rotation R matrix from $Rot_x$, $Rot_y$, and $Rot_z$ using the equations of the Craig text according to the fixed-axis method.

Now build the T matrix using R and the translations $Trans_x$, $Trans_y$, and $Trans_z$ The final T matrix represents the small translations and rotations needed to correct counter the forces and torques at the tool's coordinate system. This is suitable for the matrix $_{n+1}{}^nT$ needed for the tool CS transformation above.

The load cell should be zeroed in order to ignore preloads. This way, the above will provide reference following. For a pre-planned navigation path, setup a CAD model of the flexible component for FEA analysis with boundary conditions that match the application. Divide the pre-planned path into discrete frames, then for each frame, iteratively configure the distal end of the flexible component to match the path at that frame. Calculate the reaction forces and torques at the load cell boundary conditions of the flexible component corresponding to each frame configuration. Populate the $F_{x,y,z}$ and $Torq_{x,y,z}$ vectors with these reaction forces and torques values. This will create a sequence of target forces and torques that correspond to the sequence of path frames. Now this sequence can be input to the algorithm above and it will seek to minimize the error between the real-time load cell output and the $F_{x,y,z}$ and $Torq_{x,y,z}$ vectors.

Thus, the system translates forces into navigational commands for a robot, other manipulator (eg. Pick and place manufacturing, CNC milling), or for human manual navigation. In the case of human navigation, a human operator would be holding a tool and the flexible component of the present navigation by bending forces system would be in contact with an object with which the human operator is interacting. The nature of the interaction may be probing, machining, measuring, painting, deforming, but is not limited to physical contact. It may be scanning by laser or camera, or any other non-contact interaction.

Thus, when the system is configured to be used in a contact mode between the instrument 18 and the object 40, the instrument may be a tool for processing material, including but not limited to a drill bit or any other kind of machine tool, or a medical instrument for interacting with tissue including but not limited to a stylus, needle, syringe, isotope introducer, embosser, stamp, polisher, grinder, mill, burr, file, drill, grasper.

When the system is configured to be used in a noncontact mode between the instrument 18 and the object 40, the instrument may be any one of but not limited to, an imaging device, a scanner, a laser, paint sprayer, ink jet, radiation monitor, magnetic or electromagnetic field sensor, capacitance or inductance sensor.

The present navigation by bending forces system disclosed herein may even be attached directly to a human operator's body instead of a tool. In this embodiment, the present navigation by bending forces system can provide navigation for direct human navigation of a specific body part in almost any environment, including under water and empty space, assuming that the electronic components of the load cell are suitably protected. The only contact with an object required by the present navigation by bending forces system is contact between the flexible component 26 and the object 40. Then navigation can be achieved relative to the object.

The present navigation by bending forces system can be used for object tracking, where the present navigation by bending forces outputs seek to maintain one position and orientation relative to the object as the object may move about. In addition, the Nay-by-Bending-Forces system can provide navigation in which the outputs of the present navigation by bending forces represent relatively positions and orientations that change relative to the object. Both of these applications are supported by the general present navigation by bending forces algorithm described herein.

In the first application of simple object tracking, in which the present navigation by bending forces system outputs seek to maintain one position and orientation relative to a possibly moving object, the output of the load cell 22 can be biased (i.e. tared to zero values) at a reference position relative to the object/patient being tracked. In this way, the forces and torques in the flexible object are biased to zero. The system will subsequently maintain this position relative to the object/patient as the object/patient moves.

In the second application, in which the present navigation by bending forces system outputs provide navigation relative to an object, a pre-planned pathway relative to the object/patient can be achieved by inputting a pre-calculated sequence of forces/torques that correspond to relative positions along the pre-planned pathway. In this way, the system will be navigated with respect to the object/patient, allowing different locations on the object/patient's surface to be visited by the tool/instrument/manipulator.

Figure 6:
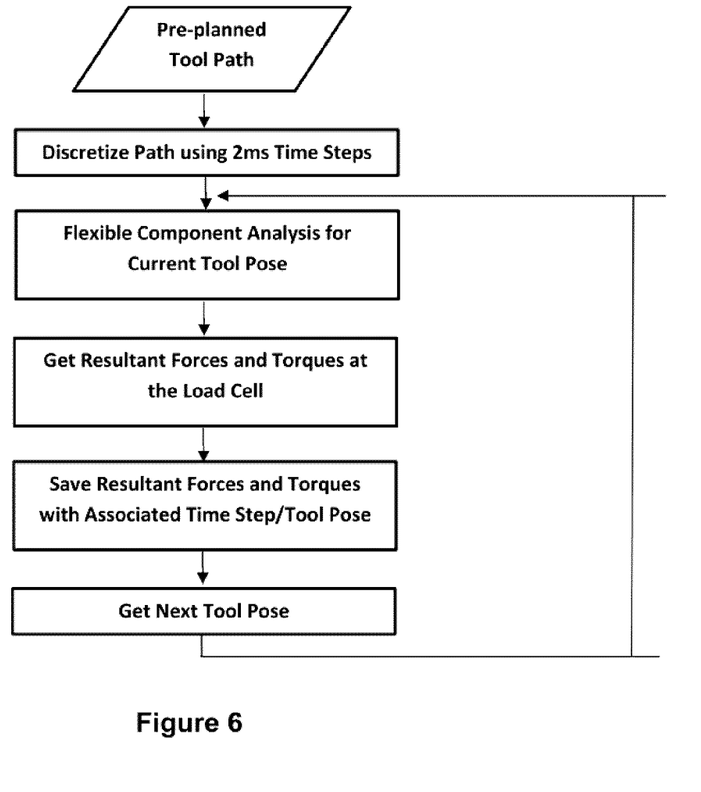
FIG. 6 shows a flow chart for a non-limiting implementation of the navigation route calculation phase.

More particularly, referring to FIG. 6, a pre-planned desired tool path is represented as a series of discrete poses at 2 millisecond steps (although this method is not limited to 2 millisecond steps as will be appreciated by those skilled in the art. At each time step, the predictable forces and torques at the load cell are calculated using a Finite Element Analysis (FEA) method or other suitable mathematical model or calculation. This is iterated for all time steps and the final sequence is saved for later input to the real-time navigation algorithm.

It is important to note that the object tracking and navigation methods can be used together, since even when navigating a pre-planned pathway, any departure from the biased reference forces/torques will automatically trigger the system to correct its relative position. This would occur when the object/patient moves for any reason. No alteration or switching of algorithms is required. It is also important to note that in the simple object tracking application, where movement relative to the object is not planned or desired, the path pre-planning aspects of the algorithm may be skipped or not implemented.

In other words, the real-time software of the navigation method is the same as the object following method. The difference is that object following method uses fixed force values for the algorithm's inputs. In contrast, the navigation method varies the forces to the inputs, thus causing the algorithm to hunt for different forces, and thus causing it to move about the object.

The present navigation by bending forces method and system disclosed herein exhibits several significant advantages and unique features compared to current tracking navigation systems. First, the present navigation by bending forces system of tracking patient anatomy does not require a clear line of sight as optical tracking systems do in order to "see" their targets.

As noted above, current tracking systems require one or more components to be rigidly mounted to the patient's bones of interest requiring that stab incisions are made in order to gain access to bone so that tracking targets can be drilled into the bones. The present navigation system does not require any additional stab incisions. The flexible component is fixed to an already exposed region of bone within the surgical exposure.

In terms of cost, the present navigation by bending forces system uses hardware including one or more small 6 dof load cells and one or more flexible components for attachment to bone. A typical load cell costs about $3000. The cost of the flexible component can be negligible if it is a simple metal strip. If the flexible component is a patient-specific mount which includes a flexible section, then its cost will likely be in the range of $100 to $500 based on 3D printing methods currently available. This is contrasted with current tracking systems that cost $100,000 or more mentioned previously.

Further, as noted above, tracking targets of current tracking systems require occasional replacement due to breakage and wear from being inside of the surgical field. Typically passive retro-reflective targets must be discarded and replaced after each surgery. In contrast, the present navigation-by-bending-forces system requires that only the flexible component(s) be sterilized or replaced, as the rest of the system, including the load cell(s), can be covered by plastic as is done with most robotic surgical systems. Depending on the installation or application requirements, if it is desired to retain the flexible component(s), then they may also be covered with plastic using current techniques. The flexible component(s) can be placed with standard operating tools for autoclave sterilization, or any other common and inexpensive sterilizing method.

It is noted that most surgical procedures can begin immediately following incision and exposure. However, the most common surgical tracking systems are optical and require some setup of the camera for line of sight, and significant setup of the tracking targets for installation into bone, as described in above. In contrast, the present navigation-by-bending-forces system requires only the attachment of one or more flexible components to the already exposed bony area and in a procedure where a robot is already used, this setup can be very rapid.

The inherent accuracy of the navigation system disclosed herein can surpass current navigation technology because the resolution of the fundamental load cell technologies, such as foil strain gauges, have infinite resolution. In contrast, most current tracking technologies have a fixed resolutions as noted above.

Finally, the navigation system disclosed herein does not suffer interference from electromagnetic, radio, sonic, or light sources while current tracking systems, based on electromagnetic, optical, or ultrasonic signals are susceptible to interference from one or more of those sources. In particular, electromagnetic systems can also be impacted by metal surgical tools, operating table, and other metallic objects.

Therefore what is claimed is:

1. A system for tracking an instrument with respect to an object, comprising:
 a) a motive source, wherein a proximal end of said instrument is attachable to said motive source and movable by said motive source;
 b) a load cell fixed in a known position with respect to said proximal end of said instrument when it is attached to said motive source;
 c) a flexible component having a proximal end attached to said load cell, said flexible component having a distal end rigidly attached to said object being tracked and the flexible component experiences forces which are measured by said load cell which depend on the pose of said instrument with respect to said object; and
 d) a computer controller connected to said load cell for receiving an output from said load cell, said output from said load cell including said forces that are experienced by the flexible component due to the pose of said instrument with respect to said object, said computer controller programmed with instructions to translate said forces that are experienced by said flexible component into navigational commands for said motive source to maintain said instrument in a preselected pose with respect to said object.

2. The system according to claim 1, wherein said instrument is any one of a contact device configured to contact said object and a non-contact device configured to be spaced away from said object.

3. The system according to claim 2, wherein said instrument is a contact device, said contact device being any one of a tool for processing material, or a medical instrument for interacting with tissue comprising one of a stylus, needle, syringe, isotope introducer, embosser, stamp, polisher, grinder, mill, burr, file, drill and grasper.

4. The system according to claim 2, wherein said instrument is a non-contact device said non-contact device being any one of an imaging device, a scanner, a laser, paint sprayer, ink jet, radiation monitor, magnetic or electromagnetic field sensor, capacitance or inductance sensor.

5. The system according to claim 1, wherein said motive source is provided by a robot having an end effector to which said instrument is attached.

6. The system according to claim 1, wherein said motive source is provided by a human operator to which said instrument is connected.

7. A system for navigating an instrument with respect to an object, comprising:
 a) a motive source, wherein a proximal end of said instrument is attachable to said motive source and movable by said motive source;
 b) a load cell fixed in a known position with respect to said proximal end of said instrument when it is attached to said motive source;
 c) a flexible component having a proximal end attached to said load cell, said flexible component having a distal end rigidly attached to said object being tracked and the flexible component experiences forces which are measured by said load cell which depend on the pose of said instrument with respect to said object; and
 d) a computer controller connected to said load cell for receiving an output from said load cell, said output from said load cell including said forces that are experienced by the flexible component due to the pose of said instrument with respect to said object said computer controller, said computer controller being pre-programmed with a pre-selected navigation route, wherein said computer controller is programmed with instructions to translate said navigation route into a series of poses of said instrument with respect to said object at discrete intervals, and calculate the predicted forces experienced by the flexible component onto said load cell at each of said poses in said series of poses said computer controller being programed to compare the forces measured by said load cell to said predicted forces of a current pose of said series of poses and output navigational commands for said motive source to correct the error between the predicted forces of said current pose and said measured forces, and said computer controller being programed to change the current pose to a next pose of said series of poses when said forces measured by said load cell are the same as the predicted forces of said current pose.

8. The system according to claim 7, wherein said instrument is any one of a contact device configured to contact said object and a non-contact device configured to be spaced away from said object.

9. The system according to claim 8, wherein said instrument is a contact device, said contact device being any one of a tool for processing material, or a medical instrument for interacting with tissue comprising one of a stylus, needle, syringe, isotope introducer, embosser, stamp, polisher, grinder, mill, burr, file, drill and grasper.

10. The system according to claim 8, wherein said instrument is a non-contact device said non-contact device being any one of an imaging device, a scanner, a laser, paint sprayer, ink jet, radiation monitor, magnetic or electromagnetic field sensor, capacitance or inductance sensor.

11. The system according to claim 8, wherein said motive source is provided by a robot having an end effector to which said instrument is attached.

12. The system according to claim 8, wherein said motive source is provided by a human operator to which said instrument is connected.

13. The system according to claim 9, wherein said motive source is provided by a robot having an end effector to which said instrument is attached.

14. The system according to claim 9, wherein said motive source is provided by a human operator to which said instrument is connected.

15. The system according to claim 10, wherein said motive source is provided by a robot having an end effector to which said instrument is attached.

16. The system according to claim 10, wherein said motive source is provided by a human operator to which said instrument is connected.

17. The system according to claim 2, wherein said motive source is provided by a robot having an and effector to which said instrument is attached.

18. The system according to claim 2, wherein said motive source is provided by a human operator to which said instrument is connected.

19. The system according to claim 3, wherein said motive source is provided by a robot having an and effector to which said instrument is attached.

20. The system according to claim 3, wherein said motive source is provided by a human operator to which said instrument is connected.

21. A system for navigating an instrument with respect to an object, comprising:
  a) a motive source, wherein a proximal end of said instrument is attachable to said motive source and movable by said motive source;
  b) a load cell fixed in a known position with respect to said proximal end of said instrument when it is attached to said motive source;
  c) a flexible component having a proximal end attached to said load cell, said flexible component having a distal end rigidly attached to said object being tracked and the flexible component experiences forces which are measured by said load cell which depend on the pose of said instrument with respect to said object; and
  d) a computer controller connected to said load cell for receiving an output from said load cell, said output from said load cell including said forces experienced by the flexible component due to the pose of said instrument with respect to said object, said computer controller being programmed with a series of poses comprising at least one poses, said computer controller being programed to calculate the predicted forces experienced by the flexible component at each of said at least one pose in said series of poses, said computer controller being programed to compare said forces measured by said load cell to said predicted forces of a target pose, wherein said target pose is a member of said series of poses, and if there is any error between said forces measured by said load cell and said predicted forces of said target pose, outputting navigational commands to reduce the error between said forces measured by said load cell and said predicted forces of said target pose.

22. The system according to claim 21, wherein said series of poses compromises one pose, and said one said pose is said target pose.

23. The system according to claim 21, wherein said series of poses comprises a plurality of poses, wherein one of said plurality of poses is said target pose, and if there is no error between said forces measured by said load cell and said predicted forces of said target pose, changing said target pose to a next pose of said series of poses.

24. The system according to claim 21, wherein said instrument is any one of a contact device configured to contact said object and a non-contact device configured to be spaced away from said object.

25. The system according to claim 24, wherein said instrument is a contact device, said contact device being any one of a tool for processing material, or a medical instrument for interacting with tissue comprising one of a stylus, needle, syringe, isotope introducer, embosser, stamp, polisher, grinder, mill, burr, file, drill and grasper.

26. The system according to claim 24, wherein said instrument is a non-contact device said non-contact device being any one of an imaging device, a scanner, a laser, paint sprayer, ink jet, radiation monitor, magnetic or electromagnetic field sensor, capacitance or inductance sensor.

27. The system according to claim 21, wherein said motive source is provided by a robot having an end effector to which said instrument is attached.

28. The system according to claim 21, wherein said motive source is provided by a human operator to which said instrument is connected.

* * * * *